United States Patent
Taylor et al.

[11] Patent Number: 5,925,787
[45] Date of Patent: Jul. 20, 1999

[54] PRODUCTION OF KETO ACIDS

[75] Inventors: James Philip Taylor, Macclesfield; William Walker; John Whitworth, both of Manchester; Michael Heneghan, Salford, all of United Kingdom

[73] Assignee: Ciba Specialty Chemicals Corporation, Tarrytown, N.Y.

[21] Appl. No.: 09/005,157

[22] Filed: Jan. 9, 1998

[30] Foreign Application Priority Data

Jan. 9, 1997 [GB] United Kingdom ............... 9700376

[51] Int. Cl.$^6$ .................................................. C07C 229/52
[52] U.S. Cl. .................................................. 562/441
[58] Field of Search ............................................. 562/441

[56] References Cited

U.S. PATENT DOCUMENTS 5,371,285  12/1994  Kondo et al. ............................ 562/441

FOREIGN PATENT DOCUMENTS 0176161   4/1986  European Pat. Off. .
0511019  10/1992  European Pat. Off. .

OTHER PUBLICATIONS

Derwent Abstract 75–00537W.
Derwent Abstract 91–181444.
Derwent Abstract 91–122582.
Derwent Abstract 91–112648.
Derwent Abstract 91–358425.
Derwent Abstract 84–130440.
Derwent Abstract 86–221316.

*Primary Examiner*—Brian M. Burn
*Assistant Examiner*—Brian J. Davis
*Attorney, Agent, or Firm*—Kevin T. Mansfield

[57] ABSTRACT

A method for the production of a keto acid having the general formula

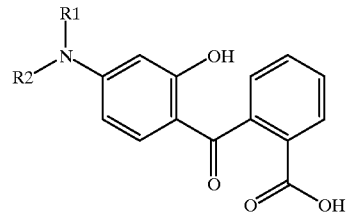

wherein R1 and R2 independently represent a straight or branched chain alkyl of 1–18 carbon atoms, a cycloalkyl of 4–8 carbon atoms or a phenyl, each of which may be substituted by at least one substituent selected from the group consisting of halogen atoms and alkyls having 1–4 carbon atoms, an aralkyl of 7–10 carbon atoms, alkoxyalkyl having 2–20 carbon atoms, tetrahydrofuryl alkyl, alkylcarboxy alkyl, alkylcarboxy benzyl, or R1 and R2 together with the adjacent nitrogen atom may form a heterocyclic ring, or one of $R_1$ and $R_2$ is hydrogen, but R1 and R2 may not simultaneously be methyl or ethyl or benzyl which comprises reacting a m-amino phenol having the general formula

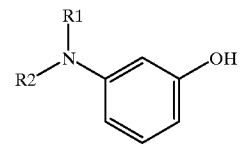

wherein R1 and R2 are the same as above, with phthalic anhydride, in an organic solvent in an amount of less than 0.5 parts by weight per part of m-amino phenol.

8 Claims, No Drawings

PRODUCTION OF KETO ACIDS

FIELD OF THE INVENTION

The invention relates to a method of producing keto acids. Such keto acids are useful intermediates for the production of fluoran compounds used as dyestuff in pressure or heat—sensitive recording.

PRIOR ART

The keto acids have previously been produced by the reaction of N, N-dialkylaminophenol with phthalic anhydride in a molar ratio of 0.5–2.0. The synthesis has been performed in the presence of an inactive solvent such as toluene, xylene or tetrahydrofuran, at a temperature of 80–150° C., as a solution or slurry dependant on the nature of the N, N-dialkyl amino phenol. Solvent has been used in a ratio of 0.5–5.0 w/w with respect to N, N-dialkylaminophenol. The volume of solvent used can cause loss of yield due to the solubility of the product keto acid in the solvent. The disposal of large amounts of solvent poses significant economic and ecological problems.

SUMMARY OF INVENTION

It is therefore, an object of this invention to provide a method of producing keto acids using a reduced amount of solvent.

The invention provides an improved method for the production of a keto acid having the general formula of

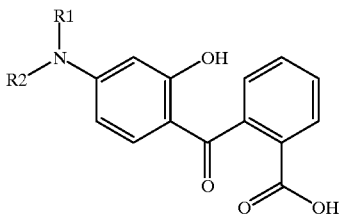

wherein R1 and R2 independently represent a straight or branched chain alkyl of 1–18 carbon atoms, a cycloalkyl of 4–8 carbon atoms or a phenyl both of which may be substituted by at least one substituent selected from the group consisting of halogen atoms and alkyls having 1–4 carbon atoms, an aralkyl of 7–10 carbon atoms, alkoxyalkyl having 2–20 carbon atoms, tetrahydrofuryl alkyl, alkylcarboxy alkyl, alkylcarboxy benzyl, or R1 and R2 together with the adjacent nitrogen atom may form a heterocyclic ring, or one of $R_1$ and $R_2$ is hydrogen, but R1 and R2 may not simultaneously be methyl or ethyl or benzyl which comprises reacting a m-amino phenol having the general formula

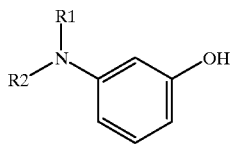

wherein R1 and R2 are the same as above, with phthalic anhydride, in an organic solvent in an amount of less than 0.5 parts by weight per part of m-amino phenol.

DETAILED DESCRIPTION OF THE INVENTION

The m-amino phenols used in the invention include, but are not limited to,

N,N-di-n-propyl aminophenol,
N,N-di-n-butyl aminophenol,
N,N-di-n-pentyl aminophenol,
N,N-di-n-hexyl aminophenol,
N,N-diisopropyl aminophenol,
N,N-disecbutyl aminophenol,
N,N-diisobutyl aminophenol,
N,N-diisoamyl aminophenol,
N-methyl-N-cyclohexyl aminophenol,
N-methyl-N-phenyl aminophenol,
N-methyl-N-(2-methylphenyl) aminophenol,
N-methyl-N-(3-methylphenyl) aminophenol,
N-methyl-N-(4-methylphenyl) aminophenol,
N-methyl-N-propyl aminophenol,
N-methyl-N-isopropyl aminophenol,
N-methyl-N-butyl aminophenol,
N-methyl-N-isobutyl aminophenol,
N-methyl-N-secbutyl aminophenol,
N-methyl-N-pentyl aminophenol,
N-methyl-N-1-methylbutyl aminophenol,
N-methyl-N-isoamyl aminophenol,
N-methyl-N-1-methylpentyl aminophenol,
N-methyl-N-hexyl aminophenol,
N-methyl-N-tetrahydrofurylmethyl aminophenol,
N-methyl-N-ethoxypropyl aminophenol,
N-methyl-N-cyclohexylmethyl aminophenol,
N-methyl-N-phenethyl aminophenol,
N-ethyl-N-cyclohexyl aminophenol,
N-ethyl-N-phenyl aminophenol,
N-ethyl-N-(2-methylphenyl) aminophenol,
N-ethyl-N-(3-methylphenyl) aminophenol,
N-ethyl- N-(4-methylphenyl) aminophenol,
N-ethyl-N-propyl aminophenol,
N-ethyl-N-isopropyl aminophenol,
N-ethyl-N-butyl aminophenol,
N-ethyl-N-isobutyl aminophenol,
N-ethyl-N-secbutyl aminophenol,
N-ethyl-N-pentyl aminophenol,
N-ethyl-N-1-methylbutyl aminophenol,
N-ethyl-N-isoamyl aminophenol,
N-ethyl-N-1-methylpentyl aminophenol,
N-ethyl-N-hexyl aminophenol,
N-ethyl-N-tetrahydrofurylmethyl aminophenol,
N-ethyl-N-ethoxypropyl aminophenol,
N-ethyl-N-cyclohexylmethyl aminophenol,
N-ethyl-N-phenethyl aminophenol,
N-propyl-N-cyclohexyl aminophenol,
N-propyl-N-phenyl aminophenol,
N-propyl-N-(2-methylphenyl) aminophenol,
N-propyl-N-(3-methylphenyl) aminophenol,
N-propyl-N-(4-methylphenyl) aminophenol,
N-propyl-N-isopropyl aminophenol,
N-propyl-N-butyl aminophenol,
N-propyl-N-isobutyl aminophenol,
N-propyl-N-secbutyl aminophenol,
N-propyl-N-pentyl aminophenol,
N-propyl-N-1-methylbutyl aminophenol,
N-propyl-N-isoamyl aminophenol,
N-propyl-N-1-methylpentyl aminophenol,
N-propyl-N-hexyl aminophenol,
N-propyl-N-tetrahydrofurylmethyl aminophenol,
N-propyl-N-ethoxypropyl aminophenol,
N-propyl-N-cyclohexylmethyl aminophenol,
N-propyl-N-phenethyl aminophenol,
N-butyl-N-cyclohexyl aminophenol,
N-butyl-N-phenyl aminophenol,
N-butyl-N-(2-methylphenyl) aminophenol, N-butyl-N-(3-methylphenyl) aminophenol,
N-butyl-N-(4-methylphenyl) aminophenol,
N-butyl-N-propyl aminophenol,
N-butyl-N-isopropyl aminophenol,
N-butyl-N-isobutyl aminophenol,
N-butyl-N-secbutyl aminophenol,
N-butyl-N-pentyl aminophenol,
N-butyl-N-1-methylbutyl aminophenol,
N-butyl-N-isoamyl aminophenol,
N-butyl-N-1-methylpentyl aminophenol,
N-butyl-N-hexyl aminophenol,
N-butyl-N-tetrahydrofurylmethyl aminophenol,
N-butyl-N-ethoxypropyl aminophenol,
N-butyl-N-cyclohexylmethyl aminophenol,
N-butyl-N-phenethyl aminophenol,
N-phenyl aminophenol
N-2-methylphenyl aminophenol
N-3-methylphenyl aminophenol
N-4-methylphenyl aminophenol
N-cyclohexyl aminophenol
3-N-pyrrolidinyl phenol.
3-N-(2-methylpyrrolidinyl) phenol.
3-N-(3-methylpyrrolidinyl) phenol.
3-N-morpholinyl phenol.
3-N-piperidinyl phenol
3-N-(2-methylpiperidinyl) phenol
3-N-(3-methylpiperidinyl) phenol.
3-N-(4-methylpiperidinyl) phenol.

For the reaction of the m-aminophenol derivative, as above mentioned, with phthalic anhydride, the latter is usually used in an amount of 0.5–2.0 moles per mole of the m-aminophenol derivative. The ratio of solvent to m-aminophenol derivative may be from 0 to 0.45 parts by weight. Preferably a solvent is used. The quantity of solvent chosen is dependant on the nature of the m-aminophenol derivative. The amount of solvent used is determined so that the reaction mass remains mobile throughout the course of the reaction, but so that the reaction is carried out in a slurry.

The organic solvents when used include, for example, an aromatic hydrocarbon of 6–10 carbon atoms such as benzene, toluene or xylene, an aliphatic hydrocarbons of 8–12 carbon atoms such as octane, isooctane, or decane, a halogenated hydrocarbon of 2–8 carbon atoms, aliphatic, cycloaliphatic or aromatic, such as perclene, chlorobenzene or dichlorobenzene, ethers such as tetrahydrofuran, dibutyl ether or diphenylether, among which are especially preferred aromatic hydrocarbons or ethers.

By way of an example, the reaction of N, N-di-n-butyl-m-aminophenol with phthalic anhydride may be carried out in the absence of solvent or in the presence of an aromatic hydrocarbon such as benzene, toluene or xylene, the preferred amount of solvent being in the range 0–0.45 parts by weight with respect to the N, N-di-n-butyl-m-aminophenol.

The reaction is effected at an elevated temperature, preferably in the range of 60–120° C. for a period of 3–40 hours. The reaction time and temperature are chosen so as to achieve a suitable balance between length of reaction and the amount of rhodamine type side products that are produced. The amount of rhodamine produced increases at higher temperatures. After the reaction, the reaction mixture is cooled to 0–60° C., most preferably 20–40° C.

Dependant on the viscosity of the reaction mixture at this stage, a secondary solvent may be added to the reaction mixture to maintain mobility.

There may be used as the secondary solvent, for example, an aromatic hydrocarbon of 6–10 carbon atoms such as benzene, toluene or xylene, an aliphatic hydrocarbons of 5–12 carbon atoms such as pentane, octane, isooctane, or decane, a halogenated aliphatic, cycloaliphatic or aromatic hydrocarbon of 2–8 carbon atoms such as perclene, chlorobenzene or dichlorobenzene, ethers such as tetrahydrofuran, dibutyl ether or diphenylether, alcohols such as methanol, ethanol, propanols such as isopropanols or butanols such as n-butanol. There may also be used a mixture of the alcohol with water or a mixture of the alcohol with a hydrocarbon solvent.

The crude keto acid derivative may be recovered from the reaction mixture by filtration, or by diluting the mixture with a solvent in which the derivative is barely soluble and recovering the precipitated derivative by filtration, or by extracting the derivative with an aqueous alkaline solution and precipitating it with acid, or by forming the sodium salt of the derivative, isolating the salt and precipitating it with acid.

As above set forth the reaction of the m-aminophenol derivative with the phthalic anhydride is carried out in the minimum of organic solvent thus reducing the economic and environmental costs of the process.

The invention will now be described in more detail with reference to examples, however, the invention is not limited to the examples.

EXAMPLE 1

An amount of 132.6 g (0.6 mol) of N,N-dibutylaminophenol, 115.5 g (0.78 mol) phthalic anhydride and 57.9 g of toluene are placed in a reactor, and stirred whilst the reaction mass is heated to 90° C. over 2 hours and then heated to 95° C. and stirred at this temperature for 12 hours. Liquid chromatographic analysis shows 90% conversion to the keto acid.

Once the reaction is complete, the reaction mass is cooled to 55° C. over 2 hours, methanol 72.6 g is added and the reaction mass cooled to 20° C. and stirred for 1 hour. The product, 4-N, N-dibutylamino-2-hydroxy-2'-carboxy benzophenone is isolated by filtration. The crude product is washed with methanol to yield the pure keto acid. The product contained 0.21% rhodamine as determined by UV absorbance.

EXAMPLE 2

An amount of 44.2 g (0.2 moles) of N,N-dibutylaminophenol and 19.6 g (0.133 moles) of phthalic anhydride are placed in a reactor and stirred at to 90–95° C. for 13 hours. Liquid chromatographic analysis shows 92% conversion to the keto acid. After the reaction, the reaction mass is cooled to 50° C., methanol 24 g is added and the reaction mass cooled to 20° C. and stirred for 1 hour. The product, 4-N,N-dibutylamino-2-hydroxy-2'-carboxy benzophenone, is isolated by filtration. The crude product is washed with methanol to yield the pure keto acid. The product contains 0.15% rhodamine as determined by UV absorbance.

EXAMPLE 3

An amount of 8.4 g (0.041 mol) of N-ethyl-N-isoamylaminophenol and 4.2 g (0.0224 mol) phthalic anhydride are placed in a reactor and stirred at 90° C. for 5 hours. Liquid chromatographic analysis shows 90% conversion to the 4-N-ethyl-N-isoamylamino-2-hydroxy-2'-carboxybenzophenone.

We claim:

1. A method for the production of a keto acid having the general formula of

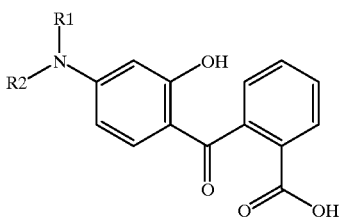

wherein R1 and R2 independently represent a straight or branched chain alkyl of 1–18 carbon atoms, a cycloalkyl of 4–8 carbon atoms or a phenyl both of which may be substituted by at least one substituent selected from the group consisting of halogen atoms and alkyls having 1–4 carbon atoms, an aralkyl of 7–10 carbon atoms, alkoxyalkyl having 2–20 carbon atoms, tetrahydrofuryl alkyl, alkylcarboxy alkyl, alkylcarboxy benzyl, or R1 and R2 together with the adjacent nitrogen atom may form a heterocyclic ring, or one of $R_1$ and $R_2$ is hydrogen, but R1 and R2 may not simultaneously be methyl or ethyl or benzyl which comprises reacting a m-amino phenol having the general formula

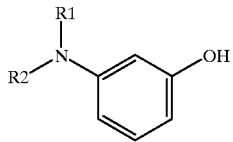

wherein R1 and R2 are the same as above, with phthalic anhydride, in an organic solvent in an amount of 0 to 0.45 parts by weight per part of m-amino phenol.

2. The method of claim 1 in which the solvent is an aromatic hydrocarbon of 6–10 carbon atoms, an aliphatic hydrocarbon of 8–12 carbon atoms, a halogenated hydrocarbon of 2–8 carbon atoms, or an ether.

3. The method of claim 1 which is carried out at a temperature of from 60 to 120° C.

4. The method of claim 1 in which the m-amino phenol is selected from N, N-di-n-propyl aminophenol, N, N-di-n-butyl aminophenol, N, N-di-n-pentyl aminophenol, N, N-di-n-hexyl aminophenol, N, N-diisopropyl aminophenol, N, N-diisobutyl aminophenol, N, N-diisoamyl aminophenol, N-ethyl-N-cyclohexyl aminophenol, N-ethyl-N-isoamyl phenol, N-ethyl-N-cyclohexylmethyl aminophenol, N-phenyl-N-ethyl aminophenol and 3-pyrrolidinol phenol.

5. The method of claim 1 in which, after the reaction, the reaction mixture is cooled to a temperature from 0 to 60° C.

6. The method of claim 5 in which, after cooling, a secondary solvent is added to the reaction mixture to maintain mobility.

7. The method of claim 6 in which the secondary solvent is an aromatic hydrocarbon of 6–10 carbon atoms, an aliphatic hydrocarbon of 5 to 12 carbon atoms, a halogenated hydrocarbon of 2–8 carbon atoms, an ether or an alcohol.

8. A method as claimed in claim 1 which is carried out in the absence of solvent.

* * * * *